US006740319B2

United States Patent
Aldrich

(10) Patent No.: US 6,740,319 B2
(45) Date of Patent: May 25, 2004

(54) CHEMICAL ATTRACTANTS FOR YELLOWJACKET WASPS

(75) Inventor: Jeffrey R. Aldrich, Adelphi, MD (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/207,770

(22) Filed: Jul. 31, 2002

(65) Prior Publication Data

US 2003/0109581 A1 Jun. 12, 2003

Related U.S. Application Data

(60) Provisional application No. 60/308,601, filed on Jul. 31, 2001.

(51) Int. Cl.$^7$ ............................................. A01N 25/34
(52) U.S. Cl. .................. 424/84; 424/405; 424/409; 424/411; 514/546; 514/557; 514/703; 514/724; 514/739; 514/693
(58) Field of Search ............................. 424/405, 410, 424/84, 409, 411; 514/739, 546, 703, 557, 724, 919, 693

(56) References Cited

U.S. PATENT DOCUMENTS 5,676,960 A * 10/1997 Myles ........................ 424/410
6,083,498 A * 7/2000 Landolt ........................ 424/84

FOREIGN PATENT DOCUMENTS

DE  4012224  * 10/1991

OTHER PUBLICATIONS

Aldrich et al Identification of a New Predaceous Stink Bug pheromone—Experientia 42(5), 583–5, '86.*

* cited by examiner

Primary Examiner—Neil S. Levy
(74) Attorney, Agent, or Firm—John D. Fado; Evelyn M. Rabin

(57) ABSTRACT

A combination of volatile components which act synergistically to effectively attract yellowjackets in the Vespula species group is provided. A preferred formulation includes (E)-2-hexenal and linalool in the first component (A) and acetic acid and isobutanol in the second component (B). The two components are combined such that the vapors of the components blend to effectively attract the targeted yellowjackets. A dispenser may be utilized to release the vapors and may also be included within a trap to provide a means for monitoring or controlling the insects.

15 Claims, 1 Drawing Sheet

US 6,740,319 B2

CHEMICAL ATTRACTANTS FOR YELLOWJACKET WASPS

BACKGROUND OF THE INVENTION

1. Field of the Invention

The present invention relates to chemical attractants for yellowjacket wasps (Vespula species) and to compositions and methods for attracting, trapping and/or killing adult yellowjackets.

2. Description of the Relevant Art

Chemical attractants for some species of yellowjackets and wasps have been reported. Eddy et al. (U.S. Pat. No. 3,912,810) describe a method of attracting yellowjackets using an ester having an alcohol and an acid moiety and having a chain length of from 10 to 12 carbon atoms. 2,4-Hexadienyl butyrate, 2,4-hexadienyl propionate and 2,4-hexadienyl isobutyrate were shown to attract *V. pensylvanica* (Davis et al. 1967. *J. Med. Entomol.* vol. 4, pp. 275–280) as well as heptyl butyrate (Davis et al. 1969. *J. Econ. Entomol.* vol. 62, p. 1245; Davis et al. 1973. *Environmental Entomol.* vol. 2, pp. 569–571; MacDonald et al. 1973. *Environmental Entomol.* vol. 2, pp. 375–379) and octyl butyrate (Davis et al. 1972. *Environmental Entomol.* vol. 1, p. 673; McGovern et al. 1970. *J. Econ. Entomol.* vol. 63, pp. 1534–1536). Chemical attractants for yellowjackets and wasps have also been described by Landolt, P. J. (1998. *Environmental Entomol.* vol. 27, no. 4; Landolt, P. J., U.S. Pat. No. 6,083,498, 2000) and include compositions of vapor blends of acetic acid and one or more of isobutanol, racemic 2-methyl-1-butanol, S-(−)-2-methyl-1-butanol, 2-methyl-2-propanol, heptyl butyrate and butyl butyrate. Aldrich et al. (1986. *Experientia*. vol. 42, pp. 583–585) identified components of the pheromone of the predaceous spined soldier bug which attract eastern yellowjacket (and related species) workers and queens: mixtures of either (E)-2-hexenal and α-terpineol or (E)-2-hexenal and linalool. In addition, various yellowjacket traps are commercially available which require baits based on sugar or pet food meat products.

Heptyl butyrate is an effective attractant for the western yellowjacket which is the main nuisance species in the western United States, however, neither heptyl butyrate nor related compounds are effective attractants for eastern species. The combination of acetic acid with isobutanol or similar alcohols is a more effective attractant for yellowjackets and paper wasps common in the eastern U.S., but this blend also attracts substantial numbers of beneficial wasps which are usually not harmful to humans or animals. Thus, although there are attractants available, the search has continued for effective attractants which increase the attraction of only nuisance species of yellowjacket wasps.

SUMMARY OF THE INVENTION

I have discovered mixtures of volatile chemicals that attract nuisance species of yellowjacket wasps. The mixtures were shown to attract wasps in the Vespula species group (which includes *V. maculifrons, V. germanica, V. vulgaris* and *V. flavopilosa*) and to greatly synergize an acetic acid/isobutanol blend. In accordance with this discovery, it is an object of the invention to provide chemical compositions which are effective attractants for nuisance species of yellowjacket wasps.

It is also an object of the invention to provide traps for yellowjacket wasps which utilize the attractant compositions.

It is a further object of the invention to provide a method effective for attracting, controlling and/or monitoring yellowjacket wasps.

Other objects and advantages of the invention will become readily apparent from the following description.

DETAILED DESCRIPTION OF THE INVENTION

Figure 1:
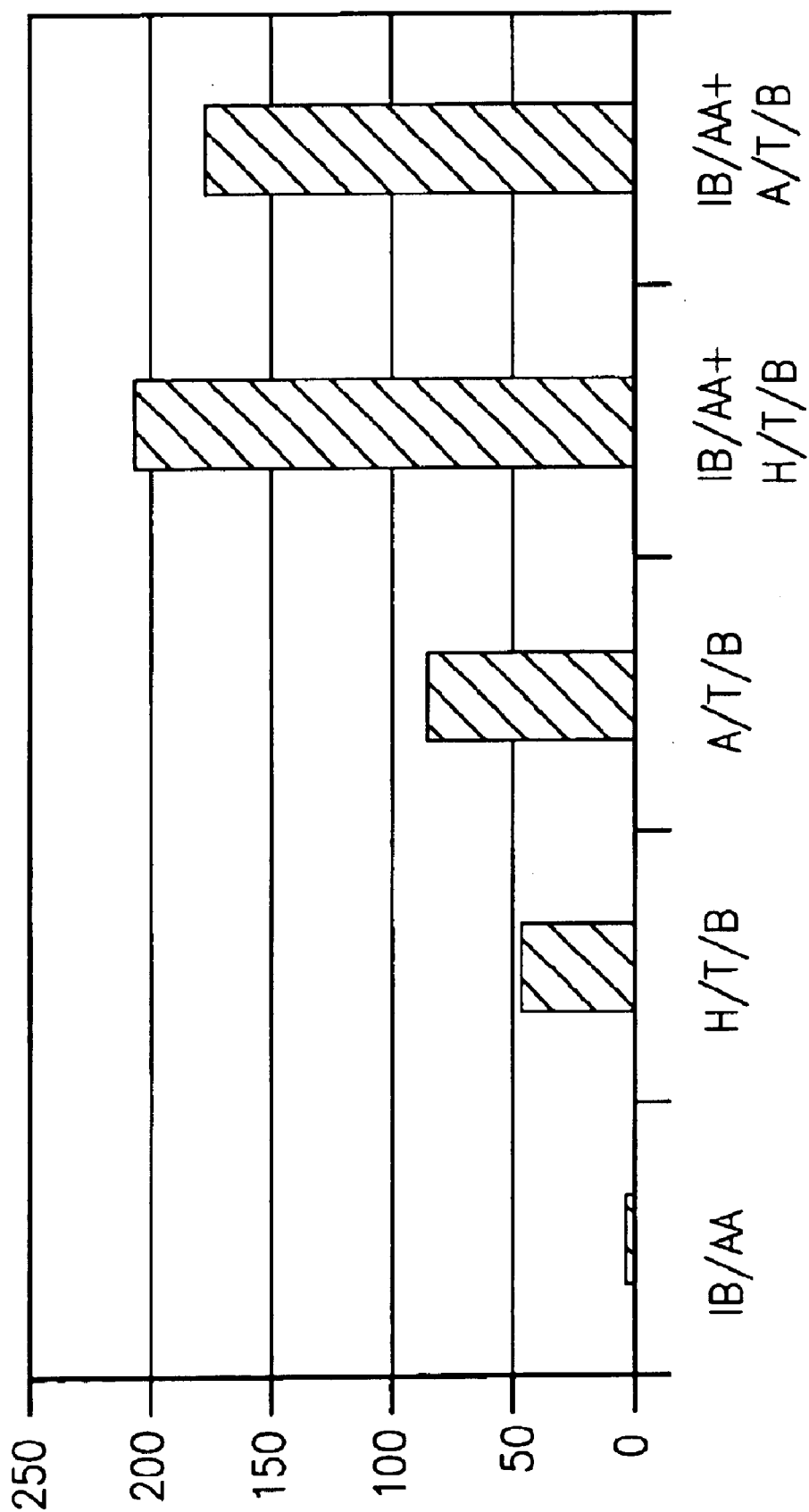
FIG. 1 shows the total captures of *Vespula maculifrons* (eastern yellowjacket) in 3 traps/treatment deployed over 7 days in September at the Beltsville Area Research Center (BARC), Beltsville, Md.

Yellowjackets are generally considered highly beneficial insects because they prey on a variety of insect pests. When disturbed, however, they can inflict painful, potentially life-threatening stings. For example, eastern and German yellowjackets make nests in the ground that, if disturbed by encounters with gardeners or small children or run over by lawnmowers, may create potentially lethal situations. Most deaths in the U.S. attributed to bee stings are actually due to yellowjacket stings. There is thus an incentive to develop products which can be used effectively in efforts to control yellowjacket populations.

The composition is a combination of two components. The first component (A) is a mixture of the volatile compounds (E)-2-hexenal and either racemic α-terpineol (α,α,4-trimethyl-3-cyclohexene-1-methanol; p-menth-1-en-8-ol) or racemic linalool (3,7-dimethyl-1,6-octadien-3-ol). (E)-2-hexenal/linalool is the preferred combination. Benzyl alcohol may optionally be included. Because of its high volatility and greater reactivity, the active ingredient (E)-2-hexenal is preferably provided as an acetal of (E)-2-hexenal with an alcohol ROH where R is any substituent containing 15 or fewer carbons. Under acidic conditions, (E)-2-hexenal is released. As the molecular weight of the alkyl substituent increases, the volatility decreases, and the resulting slow release may be advantageous when considering shelf life of the composition and effective life in the field. The compounds are mixed in a ratio of approximately 1:1 (v:v), i.e. (E)-2-hexenal:terpineol/linool. When utilizing the acetal, the higher molecular weights must be accounted for in determining an effective ratio. Acidic conditions are achieved by any means well-known in the art. Since component (A) is utilized with another component which contains acetic acid, acetic acid would be a particularly convenient acidifying agent. A pH of about 6 to about 4 is effective for release of the (E)-2-hexenal from the complex. If included, benzyl alcohol is present in an amount of approximately 2% (v/v), or could be provided at high concentration (twice that of (E)-2-hexenal) if (E)-2-hexenal-dibenzyl acetal were used.

The second component, component (B) is a vapor blend or a mixture of vapor of acetic acid and one or more compounds selected from the group consisting of isobutanol, racemic 2-methyl-1-butanol, S-(−)-2-methyl-1-butanol, 2-methyl-2-propanol, heptyl butyrate and butyl butyrate; preferably isobutanol or heptyl butyrate, most preferably isobutanol (as described by Landolt, 1998, 2000, supra). The vapor mixture or blend may occur by mixing the compounds, by placing the compounds in sufficient proximity that the volatile vapors blend or by utilizing a single compound which dissociates into compounds which produce the vapor blends. Preferably, the blend is of vapors of acetic acid and isobutanol.

All compounds utilized in the attractant composition are commercially available.

The two components are combined such that the vapors blend to effectively attract the targeted yellowjackets. They may be combined as described for each individual component, i.e. the compounds may be applied separately or as mixtures so long as the volatile vapors blend. Synergistic effects have been observed, and the relative amounts which result in synergism may be affected by the particular compounds selected. A mixture of equal molar amounts of the individual compounds utilized will result in an effective attractant. In general, however, component A should be present in the combination in amounts ranging from about 20% to about 80% of the total volume (or weight), preferably about 50%, of the combined components. It should be noted that there is considerable flexibility in the system with respect to these individual amounts. As long as there is a sufficient amount of a particular compound to effectively contribute to the vapor mixture, the actual amount of that compound is not critical. Effective synergistic amounts may be readily determined experimentally by one of skill in the art by carrying out dose response protocols. These protocols are well established, however, basically they involve varying the amounts of one element at a time of a combination of elements to determine maximum, minimum and/or optimum amounts which achieve the desired result (see Landolt, 2000, supra, for a detailed description).

Typically, attractants are utilized as lures which include dispenser means for release of the attractants. Useful dispenser materials are well-known in the art and include solid supports, absorbent materials such as textiles and paper, and polymeric matrices in the form of pellets, plugs, laminates and membranes. The attractant composition may be applied as a coating, absorbed by absorbent materials or contained within polymeric matrices. Alternatively, the volatiles may be transferred from a container holding the attractant composition through the dispenser for release.

Additives, such as toxicants, feeding stimulants, extenders may also be added to lures so long as they do not interfere with the attractant activity of the composition. Interference can be experimentally evaluated by one of skill in the art by comparing the efficacy of the blend with and without the presence of a particular additive. Reductions in attractancy, such as reduced captures of wasps may be determined by standard statistical analyses. Some reduction may be considered acceptable if the additive provides a needed function. For example, lures may be combined with feeding stimulants to provide baits for yellowjackets. The addition of toxicants provides poisoned baits for killing captured yellowjackets. Extenders such as mineral oil can provide controlled release of the attractant by reducing the rate of volatilization of the vapors from the dispenser.

Environmental, seasonal, situational and other factors (temperature, wind velocity, rain, time of day and seasonal population fluctuation) may also influence the response of yellowjackets to the attractants and subsequently the number of insects actually attracted. The location for dispersal of attractants may also be important in determining amounts to be utilized, i.e. fields, woods and forests which are largely uninhabited present a different scenario from back yards which have a much higher chance of contact between humans and pets and the higher population densities of yellowjackets which can be expected due to the presence of the attractant composition.

Attractants, dispensers and/or lures are useful in combination with traps. An effective trapping system includes a trapping means and a dispenser means located within the trapping means which provides an effective attractant amount of a vapor blend of the vapors of components (A) and (B). A trapping means is any device for catching insects, particularly yellowjackets and includes, but is not limited to, a number of traps which are commercially available [sticky-wing traps (TackTrap™, Animal Repellants, Inc., Griffin, Ga.); Yellowjacket Trappit Dome traps, Agrisense, Fresno, Calif.; water traps (Rescue!®, Sterling International, Inc., Spokane, Wash.)] and which are described in the art (e.g. U.S. Pat. Nos. 5,557,880; 5,522,172; 5,501,033; 5,339,563). A preferred trap has a mixing chamber where vapors of components (A) and (B) form a blend and the vapor blend exits the trap chamber to attract yellowjackets to a chamber from which they cannot escape. The attractant components that produce the attractant vapor blend may be present as a mixture or in separate dispensers within the trap. The components also may be added directly to a drowning solution that can be used in the trap, with the vapor blend emanating from the drowning solution. Additives may be present in the drowning solution that aid in the capture and killing of attracted yellowjackets, such as detergents or wetting agents, clays, dyes and toxicants, as long as the additives do not substantially interfere with the effectiveness of the attractant blend. The trap used for the experiments described herein is described in Example 1 and consists of a bag with a baffle on the top where the insects enter. Tap water poured into the trap (about $2/3$ full) dissolves the various compounds of the attractant composition and serves to kill attracted insects by drowning. Traps may also be utilized where trapped insects are killed by toxicant-containing poison baits where the yellowjackets may consume poisoned bait.

Useful toxicants (or insecticides) for yellowjackets include organophosphorous toxicants, carbamates, inorganic toxicants and insect growth regulators. Specific compounds include dimethyl (2,2,2-trichloro-1-hydroxyethyl) phosphonate, 2,2-dichlorovinyl dimethyl phosphate and 1,2-dibromo-2,2-dichloroethyl dimethyl phosphate. Poisoned baits are provided by combining, mixing or blending toxicant with a feeding stimulant such as pet food.

Alternatively, including slow-acting insecticides or chemosterilants in the attractant and/or poison bait and allowing the yellowjacket to return to the nest may provide a more effective means of controlling yellowjacket populations than trapping. The poison bait is then fed to the brood and queen, effectively killing off the colony.

Although both components of the composition are known attractants for yellowjacket wasps (Landolt, 1998, 2000, supra and Aldrich et al., supra, both herein incorporated by reference), the combination of the two resulted in a synergistic effect which was surprising and unexpected and is shown by the following results. Field tests were carried out using lures prepared as described in Example 1. Traps baited with various prepared lures, in addition to unbaited control traps, were hung from trees or fences at three locations: Beltsville Agricultural Research Center—West (BARC—W), Beltsville, Md.; University of Maryland Apiary; and a private residence, Silver Spring, Md., with apple trees on the property. Most tests were conducted late in the season when populations of yellowjackets were greatest. After exposure in the field for varying periods of time, traps were brought to the laboratory for sorting and counting insects by species.

Chemicals used in the various blends tested are abbreviated as follows: (E)-2-hexenal diethyl acetal (A); (E)-2-hexenal (H); α-terpineol (T); linalool (L); benzyl alcohol (B); acetic acid (AA); isobutanol (IB); heptyl butyrate (HB).

In initial experiments, the equivalence of H vs. A was tested along with the synergism between IB/AA and H/T/B or A/T/B blends. Five chemical treatments in replicates of three were tested over a period of 7 days in September at BARC—W. Results are shown in FIG. 1 where it is shown that A can effectively replace H in this system and that the H/T/B and the A/T/B blends synergize the activity of the IB/AA blend to attract *V. maculifrons*. The use of acetal (A) is considered more desirable than hexenal (H) for this type of lure because of its lower volatility and greater stability.

Species specificity was also tested. Five chemical treatments were tested at the University of Maryland apiary over a seven-day period in September: IB/AA; IB/AA+H/T/B; IB/AA+A/T/B; H/T/B; A/T/B. Results, shown in Table 1, support the results of FIG. 1 and indicate the specificity of the lures. Of particular importance is the relatively low attraction of honeybees despite the fact that the test area was surrounded by hives of *A. mellifera*. It is also notable that lures containing IB/AA (treatments 1–3) captured mostly *Vespula squamosa*, a species not considered to be a nuisance pest, whereas the H/T/B and A/T/B traps (treatments 4 and 5) caught only one individual of *V. squamosa*. This test also demonstrated the uneven, localized distribution of yellowjacket species since few *V. maculifrons* were captured in this area while it was the dominant species captured at the BARC—W site.

The equivalence of T vs. L was tested along with the effect of B and the possible synergism of HB. Six chemical treatments in replicates of three were tested over a period of 9 days in September/October at BARC—W: IB/AA; HB+A/T/B; IB/AA+A/T;

TABLE 1

Captures of yellowjackets and honeybees in traps deployed at the University of Maryland apiary over 7 days in September.

| Treatment | Vm | Vs | Vg | Am |
|---|---|---|---|---|
| 1 (IB/AA) | 1 | 16 | 0 | 0 |
| 2 (IB/AA + H/T/B) | 3 | 6 | 0 | 0 |
| 3 (IB/AA + A/T/B) | 5 | 9 | 1 | 2 |
| 4 (H/T/B) | 0 | 0 | 0 | 3 |
| 5 (A/T/B) | 0 | 1 | 0 | 1 |

Vm, *Vespula maculifrons*
Vs, *Vespula squamosa*
Vg, *Vespula germanica*
Am, *Apis mellifera*

IB/AA+A/L; IB/AA+A/T/B; A/L. Results are shown in Table 2 and demonstrate that L effectively substitutes for T and that B is not essential for lure activity. The results of treatment 2 (HB+A/T/B) suggest that heptyl butyrate may act synergistically with the H or A/T/B blends. The test also corroborates earlier results indicating localized distribution of yellowjacket species since no *V. squamosa* were captured and only one individual of *V. germanica* was caught. The synergistic effect between IB/AA and the novel blends was also confirmed.

TABLE 2

Captures of yellowjackets in traps deployed at BARC-W over a period of 9 days in September/October.

| Treatment | Trap # | Vm | Vg | Vs |
|---|---|---|---|---|
| 1 (IB/AA) | 1 | 4 | 0 | 0 |
| | 8 | 4 | 0 | 0 |
| | 15 | 15 | 1 | 0 |
| | 22 | 11 | 0 | 0 |
| | | 34 | 1 | 0 |

TABLE 2-continued

Captures of yellowjackets in traps deployed at BARC-W over a period of 9 days in September/October.

| Treatment | Trap # | Vm | Vg | Vs |
|---|---|---|---|---|
| 2 (HB + A/T/B) | 2 | 57 | 0 | 0 |
| | 9 | 79 | 0 | 0 |
| | 16 | 43 | 0 | 0 |
| | 23 | 58 | 0 | 0 |
| | | 237 | 0 | 0 |
| 3 (IB/AA + A/T) | 3 | 38 | 0 | 0 |
| | 10 | 85 | 0 | 0 |
| | 17 | 97 | 0 | 0 |
| | 24 | 98 | 0 | 0 |
| | | 318 | 0 | 0 |
| 4 (IB/AA + A/L) | 4 | 52 | 0 | 0 |
| | 11 | 93 | 0 | 0 |
| | 18 | 163 | 1 | 0 |
| | 25 | 122 | 2 | 0 |
| | | 430 | 3 | 0 |
| 5 (IB/AA + A/T/B) | 5 | 43 | 0 | 0 |
| | 12 | 106 | 0 | 0 |
| | 19 | 96 | 0 | 0 |
| | 26 | 138 | 0 | 0 |
| | | 383 | 0 | 0 |
| 6 (A/L) | 6 | 22 | 0 | 0 |
| | 13 | 36 | 0 | 0 |
| | 20 | 37 | 0 | 0 |
| | 27 | 34 | 0 | 0 |
| | | 129 | 0 | 0 |

Vm, *Vespula maculifrons*
Vg, *Vespula germanica*
Vs, *Vespula squamosa*

Further tests indicated seasonal variation in yellowjacket populations. Three chemical treatments (+control) in replicates of three were tested over the period from June 27 through October 12 at BARC—W: IB/AA; IB/AA+A/L; A/L. Results are shown in Table 3. Increased populations over the time periods tested were found. Synergism between IB/AA and A/L/B was also indicated.

TABLE 3

Captures of yellowjackets in traps deployed at BARC-W from June 27 through October 12.

| | 6/27–7/13 | | 7/13–7/28 | | 8/17–10/12 | |
|---|---|---|---|---|---|---|
| Treatment | Vm | Vs | Vm | Vs | Vm | Vs |
| IB/AA | 0.2 | 0 | 0.3 | 0 | 1.4 | 0.04 |
| IB/AA + A/L/B | 2.7 | 0 | 3.0 | 0 | 8.1 | 0.22 |
| A/L/B | — | — | 0.7 | 0 | 1.1 | 0.59 |
| Control | 0 | 0 | 0 | 0 | 0.11 | 0 |

Numbers represent means/trap/week
Vm, *Vespula maculifrons*
Vs, *Vespula squamosa*

Additional experiments were carried out which tested the synergism between IB/AA and A/L/B. Three chemical treatments (+control) were tested over a period of 11 days in September at a private residence in Silver Spring, Md.: A/L/B; IB/AA; IB/AA+A/L/B. This test demonstrated that both *V. germanica* (German yellowjacket) and *V. flavopilosa* (hybrid yellowjacket) are synergistically attracted to the combination of IB/AA+A/L/B. The test also highlighted the spotty distribution of yellowjacket species; in this urban environment the German yellowjacket appears to be the dominant nuisance species.

The following example is intended only to illustrate the invention and is not intended to limit the scope of the invention as defined by the claims.

TABLE 4

Captures of yellowjackets in traps deployed at a private residence in Silver Spring, MD over a period of 11 days in September.

| Species | Control | A/L/B | IB/AA | IB/AA + A/L/B |
|---|---|---|---|---|
| V. squamosa | 5 | 4 | 8 | 34 |
| V. vidua | 0 | 2 | 0 | 0 |
| V. maculifrons | 0 | 4 | 6 | 44 |
| V. germanicax-anthic | 1 | 11 | 3 | 59 |
| V. germanica-melanic | 5 | 14 | 5 | 106 |
| V. flavopilosa | 0 | 0 | 2 | 23 |

EXAMPLE 1

Preparation of Lures

Polyvinyl chloride (PVC) plugs containing an about 16% load of volatiles were prepared. For purposes of example, lures containing (E)-2-hexenal diethyl acetal, A (Bedoukian, Inc., Danbury, Conn.) and linalool, L (Aldrich Chemicals, Milwaukee, Wis.) are described.

PVC resin (200 g) was mixed thoroughly with 60 ml dioctyl phthalate, a blend of 30 ml of A with 20 ml of L was poured into the plasticized PVC and mixed. The material was then poured into test tubes, completely filling the tubes, and heated at 110° C. for 30 min. This process resulted in sufficient expansion of the material for the plug to be easily removed from the test tube. The PVC lure plugs (about 8 g) prepared in this manner were dropped into water inside traps (Rescue!®, Sterling International, Inc., supra) placed in the field. Optionally, as prescribed, approximately 1 ml benzyl alcohol was also added to the mixture.

The AA/IB lures (Sterling International, Inc., supra) are described in Landolt, 2000, supra, and are crystalline materials contained in a pouch placed inside the trap. Water added to begin a test dissolved the pouch to release the volatiles.

All references cited hereinabove are herein incorporated by reference in their entirety.

I claim:

1. An attractant composition for nuisance species of yellowjackets comprising volatile components (A) and (B) which act synergistically to attract said yellowjackets, component (A) comprising (E)-2-hexenal and racemic α-terpineol or (E)-2-hexenal and racemic linalool, and component (B) comprising acetic acid and one or more compounds selected from the group consisting of isobutanol, racemic 2-methyl-1-butanol, S-(−)-2-methyl-1-butanol, 2-methyl-2-propanol, heptyl butyrate and butyl butyrate, wherein the composition is a blend or mixture of vapors of the volatile components.

2. The composition of claim 1, wherein component (A) comprises (E)-2-hexenal and linalool.

3. The composition of claim 1, wherein component (B) comprises acetic acid and isobutanol.

4. The composition of claim 2, wherein (E)-2-hexenal and linalool are present at a ratio of approximately 1:1 (v:v).

5. The composition of claim 1, wherein component (A) is present in the composition in an amount ranging from about 20% to about 80% of the total volume.

6. The composition of claim 4, wherein component (A) is present in the composition in an amount of about 50% of the total volume.

7. The composition of any of claims 1–5, wherein said (E)-2-hexenal is provided an acetal of (E)-2-hexenal with an alcohol ROH where R is any substituent containing 15 or fewer carbon atoms.

8. A method for attracting nuisance species of yellowjackets, said method comprising providing a dispenser means which releases a vapor blend or mixture of volatile components (A) and (B) which act synergistically to attract said yellowjackets, component (A) comprising (E)-2-hexenal and α-terpineol or (E)-2-hexenal and linalool, and component (B) comprising acetic acid and one or more compounds selected from the group consisting of isobutanol, racemic 2-methyl-1-butanol, S-(−)-2-methyl-1-butanol, 2-methyl-2-propanol, heptyl butyrate and butyl butyrate.

9. The method of claim 8, wherein component (A) comprises (E)-2-hexenal and linalool.

10. The method of claim 8, wherein component (B) comprises acetic acid and isobutanol.

11. The method of claim 9, wherein (E)-2-hexenal and linalool are present in said dispenser means at a ratio of approximately 1:1 (v:v).

12. The method of claim 8, wherein component (A) is present in said dispenser means in an amount ranging from about 20% to about 80% of the total volume of the volatile components.

13. The method of claim 12, wherein component (A) is present in said dispenser means in an amount of about 50% of the total volume of the volatile components.

14. The method of any of claims 8–13, wherein said E-2-hexenal is provided by an acetal of (E)-2-hexenal with an alcohol ROH where R is any substituent containing 15 or fewer carbon atoms.

15. The method of claim 8, wherein attracted yellowjackets are trapped within a trapping means for yellowjackets which includes said dispenser means.

* * * * *